United States Patent [19]
Lunnen et al.

[11] Patent Number: 6,004,793
[45] Date of Patent: Dec. 21, 1999

[54] **METHOD FOR CLONING AND PRODUCING THE AVAI RESTRICTION ENDONUCLEASE IN *E. COLI* AND PURIFICATION OF THE RECOMBINANT AVAI RESTRICTION ENDONUCLEASE**

[75] Inventors: Keith D. Lunnen, Essex; Michael A. Dalton, Manchester; Geoffrey G. Wilson, Beverly; Shuang-yong Xu, Lexington, all of Mass.

[73] Assignee: New England Biolabs, Inc., Beverly, Mass.

[21] Appl. No.: 09/135,639

[22] Filed: Aug. 18, 1998

[51] Int. Cl.$^6$ .............................. C12N 9/22; C12N 15/70
[52] U.S. Cl. ....................... 435/199; 435/252.33
[58] Field of Search ................ 435/199, 252.33

[56] References Cited

U.S. PATENT DOCUMENTS

| 5,200,333 | 4/1993 | Wilson | 435/172.3 |
| 5,498,535 | 3/1996 | Fomenkov et al. | 435/172.3 |

OTHER PUBLICATIONS

Roberts et al, Nucl. Acids Res. 26:338–350 (1998).
Kosykh et al., Mol. Gen. Genet. 178:717–719 (1980).
Mann et al., Gene 3:97–112 (1978).
Walder et al., Proc. Nat. Acad. Sci. 78:1503–1507 (1981).
Bougueleret et al., Nucl. Acids. Res. 12:3659–3676 (1984).
Gingeras et al., Proc. Acad. Sci. USA 80:402–406 (1983).
Theriault et al., Gene 19:355–359 (1982).
Blumenthal et al., J. Bacteriol. 164:501–509 (1985).
Kiss et al., Nucl. Acids. Res. 13:6403–6421 (1985).
Szomolanyi et al., Gene 10:219–225 (1980).
Janulaitis et al., Gene 20:197–204 (1982).
Kiss et al., Gene 21:111–119 (1983).
Walder et al., J. Biol. Chem. 258:1235–1241 (1983).
Fomenkov et al., Nucl. Acids Res. 22:2399–2403 (1994).
Murray et al., Biochem. J. 159:317–322 (1976).
Ruan et al., Mol. Gen. Genet. 252:695–699 (1996).
Ruan et al., Gene 188:35–39 (1997).
Skoglund et al., Gene 88:1–5 (1990).
Birnboin et al., Nuc. Acids Res. 7:1513–1523 (1979).

*Primary Examiner*—Charles L. Patterson, Jr.
*Attorney, Agent, or Firm*—Gregory D. Williams

[57] ABSTRACT

A recombinant restriction endonuclease from *Anabaena variabilis* is provided, as well as the isolated gene which encodes it and methods for the production of the recombinant AvaI restriction endonuclease. An isolated gene encoding a modification methylase from *A. variabilis* is also provided.

5 Claims, 3 Drawing Sheets

FIG. 1 avaIM gene, 1446 bp    avaIR gene, 945 bp

FIG. 2

```
   1 ATGACTTCATTTGAGCTTGAGAGTCCAATAGAAATAAAGACTGACCCGACTGATCTTGAT
     M  T  S  F  E  L  E  S  P  I  E  I  K  T  D  P  T  D  L  D
  61 CAAGAGAGTGATTCCTTTGTACAAGAAATTTCTCGATTCAATAAAGCACTTGAGCAACGT
     Q  E  S  D  S  F  V  Q  E  I  S  R  F  N  K  A  L  E  Q  R
 121 TTTAGAGATAAGATGCGATTGCATGAAAGTTTAAGTCGAAAAATAGTTAGTTTTCAAGCT
     F  R  D  K  M  R  L  H  E  S  L  S  R  K  I  V  S  F  Q  A
 181 AATAAGTCAAAACCTCAGTATCGCTGGTTTAAATATAAAGAAGCTTTTTCAGTTGATTTG
     N  K  S  K  P  Q  Y  R  W  F  K  Y  K  E  A  F  S  V  D  L
 241 GTAAATCAGTTAATATTCGAGTACGAGAAAAAATCATTTGAGAGGATTCTTGACCCCTTC
     V  N  Q  L  I  F  E  Y  E  K  K  S  F  E  R  I  L  D  P  F
 301 GCAGGAGCAGGAACAATGCTATTTGCCTGTAGTGATGCCGGTATTCAAGCAGATGGTATA
     A  G  A  G  T  M  L  F  A  C  S  D  A  G  I  Q  A  D  G  I
 361 GAAGTGTTACCTATTGGTCAAGAGATTATTGAAGTAAGGAAAATAATCCAGCGACAATTC
     E  V  L  P  I  G  Q  E  I  I  E  V  R  K  I  I  Q  R  Q  F
 421 CGTCGAGAAGATTTTTTGAGATTGATTGAATGGTACAAACAAAAACCTTGGAATCAGCAT
     R  R  E  D  F  L  R  L  I  E  W  Y  K  Q  K  P  W  N  Q  H
 481 AATAATAGAAAATATCTTAATCGTTTAAGAATTACTGACGGAGCTTATCCTCCTGAAACA
     N  N  R  K  Y  L  N  R  L  R  I  T  D  G  A  Y  P  P  E  T
 541 GAAGCATCAATAGAGAGATTTTTATTTTCTATAGAAAAAGAGAATATTCTTGTGAAACAA
     E  A  S  I  E  R  F  L  F  S  I  E  K  E  N  I  L  V  K  Q
 601 GTTCTCCGTTTTGCTCTATTGTGTATTCTTGAATCTATCAGCTATACCCGTAAAGATGGA
     V  L  R  F  A  L  L  C  I  L  E  S  I  S  Y  T  R  K  D  G
 661 CAGTATCTACGTTGGGATAAAAGAGCATTTAGGAAAAGTGGATCAGATAAATTTGATAAA
     Q  Y  L  R  W  D  K  R  A  F  R  K  S  G  S  D  K  F  D  K
 721 GGTAAAATTCTGGATTTCGATGAAGCAATTACTGAGCAAATAAAATTAATTTTTGAATGAT
     G  K  I  L  D  F  D  E  A  I  T  E  Q  I  K  L  I  L  N  D
 781 TCCTTTGACTTAATAAGTAATACATTATTTTGTTATGGGACTCAAAGAAGTGGAATTAAT
     S  F  D  L  I  S  N  T  L  F  C  Y  G  T  Q  R  S  G  I  N
 841 TTATTTAATGCTTCATGTCTTAAAATTCTGCCTGAATTTGAGCAAGATTTTTACGACTGT
     L  F  N  A  S  C  L  K  I  L  P  E  F  E  Q  D  F  Y  D  C
 901 ATCATTACCTCTCCACCCTATTGTAATCGTTATGACTATACACGTACATACGCTCTAGAA
     I  I  T  S  P  P  Y  C  N  R  Y  D  Y  T  R  T  Y  A  L  E
 961 TTAGCTCTATTAGGTGTGGGAGAAAGAGATATAGTACAACTTAGGCAAGATATGCTGAGT
     L  A  L  L  G  V  G  E  R  D  I  V  Q  L  R  Q  D  M  L  S
1021 TGTACTGTTGAAAACAAAGAAAAGTCTCTTATTCACAATTGGCAGGAAGCATTACGCATA
     C  T  V  E  N  K  E  K  S  L  I  H  N  W  Q  E  A  L  R  I
1081 CTTGATAAACAAGAATTGTTACAAAGTATCTTGCGCTTTCTTGAGCGAGAGCTTGAAAGA
     L  D  K  Q  E  L  L  Q  S  I  L  R  F  L  E  R  E  L  E  R
1141 AAAAAACTTAATAATAACGGTATTCCTCGTATGATAAAAGGATATTTCTATGAAATGGCT
     K  K  L  N  N  N  G  I  P  R  M  I  K  G  Y  F  Y  E  M  A
1201 TGCGTTATTATAGAATGCTTTAGAGTTTTAAAAAATGGCTCACCTTTATTTATGGTAAAT
     C  V  I  I  E  C  F  R  V  L  K  N  G  S  P  L  F  M  V  N
1261 GATAATGTTCGCTATGCAGGTATTGATATTTCGGTTGATTTAATTCTTTCTAATATTGCA
     D  N  V  R  Y  A  G  I  D  I  S  V  D  L  I  L  S  N  I  A
1321 GAAGAAATTGGTTTTAATGTGGAGAAAATTCTTGTCTTACCTACTGGCAAAGGTAACAGT
     E  E  I  G  F  N  V  E  K  I  L  V  L  P  T  G  K  G  N  S
1381 AGCCAACAAATGGGGACACATGGAAGAAAGACACTTCGCAAATGTGTGTATGTTTGGAGA
     S  Q  Q  M  G  T  H  G  R  K  T  L  R  K  C  V  Y  V  W  R
1441 AAACCCTAG 1449
     K  P  *
```

FIG. 3

```
         GTGCCATATCAATATCATATTCAAAGCAATGATGATCTTGTGACTCCATATCAAGAAGTC
  1      ----------+---------+---------+---------+---------+---------+
         M  P  Y  Q  Y  H  I  Q  S  N  D  D  L  V  T  P  Y  Q  E  V
         CGAGCAGGATTTGTTGCTTTAGCTTTAGAAAGAAATCGAAAAGCAACACCATTTGTTGAG
 61      ----------+---------+---------+---------+---------+---------+
         R  A  G  F  V  A  L  A  L  E  R  N  R  K  A  T  P  F  V  E
         CAGGCAAGAGCATTAAAGATCCGAGTAAGCCAAATTGAAAGGCCTCAAGACCTTTTACAA
121      ----------+---------+---------+---------+---------+---------+
         Q  A  R  A  L  K  I  R  V  S  Q  I  E  R  P  Q  D  L  L  Q
         ATGAGGGATATTAGACCTACTCTACTAGCTGCCTCTGGGGTATCAGATAAAGCTGCTGGA
181      ----------+---------+---------+---------+---------+---------+
         M  R  D  I  R  P  T  L  L  A  A  S  G  V  S  D  K  A  A  G
         CACCTTCAAGAACAAGATAAAGTCGATGCAATAGAAGGTTTAATTCAAAACTTCCTAGAG
241      ----------+---------+---------+---------+---------+---------+
         H  L  Q  E  Q  D  K  V  D  A  I  E  G  L  I  Q  N  F  L  E
         CCTGCTGGAGAAAACTTTGTAGAAGAACTAGTTTACCGTTTCCTGCTTACGCGTGGAGAT
301      ----------+---------+---------+---------+---------+---------+
         P  A  G  E  N  F  V  E  E  L  V  Y  R  F  L  L  T  R  G  D
         ACACTTGGTGGATCAATGCGAAATGTTGGTGGTATCCTTGCTGAACGTAAATTTGCAAGA
361      ----------+---------+---------+---------+---------+---------+
         T  L  G  G  S  M  R  N  V  G  G  I  L  A  E  R  K  F  A  R
         TATATTATTTCTGCACTAACTTTATCGAATACCTCTTATAAATGGCTAGATAAAAACAGC
421      ----------+---------+---------+---------+---------+---------+
         Y  I  I  S  A  L  T  L  S  N  T  S  Y  K  W  L  D  K  N  S
         AAAACTTGGCTTAATCAACCTGATGATGATACAGACATTGAATTACGTCTTAGGGGATTA
481      ----------+---------+---------+---------+---------+---------+
         K  T  W  L  N  Q  P  D  D  D  T  D  I  E  L  R  L  R  G  L
         AGTTGGAACTTGGAGGGTAGGAATAGGACTTTCATTTATAATGTAAATGTTCCGATTGTG
541      ----------+---------+---------+---------+---------+---------+
         S  W  N  L  E  G  R  N  R  T  F  I  Y  N  V  N  V  P  I  V
         CGAAAAAACATTGATATTTGTTTGTTTGATTGCAGACAAAATGAAATTGAAAAGAATATA
601      ----------+---------+---------+---------+---------+---------+
         R  K  N  I  D  I  C  L  F  D  C  R  Q  N  E  I  E  K  N  I
         ATTTCAAACCCAAATATCTACATAGCTCTAGGTGAATTAAAGGGCGGTATTGACCCAGCA
661      ----------+---------+---------+---------+---------+---------+
         I  S  N  P  N  I  Y  I  A  L  G  E  L  K  G  G  I  D  P  A
         GGAGCAGACGAACATTGGAAAACAGCGAACAGTGCTTTAGCCAGAATCAGAACAGCATTT
721      ----------+---------+---------+---------+---------+---------+
         G  A  D  E  H  W  K  T  A  N  S  A  L  A  R  I  R  T  A  F
         GATCGGCACAGTCTTAAGCCATATACTTTTTTTGTGGGATCTGCTATAGAAAAAAGCATG
781      ----------+---------+---------+---------+---------+---------+
         D  R  H  S  L  K  P  Y  T  F  F  V  G  S  A  I  E  K  S  M
         GCAGAAGAAATTTGGCATCAACTAAATTCTGGCATTCTTACTAATGCAGCAAACCTCACT
841      ----------+---------+---------+---------+---------+---------+
         A  E  E  I  W  H  Q  L  N  S  G  I  L  T  N  A  A  N  L  T
         CAGCCTGACCAAGTTGCCTCTTTGTGCGCTTGGTTTATTCAACTTTGA
901      ----------+---------+---------+---------+--------948
         Q  P  D  Q  V  A  S  L  C  A  W  F  I  Q  L  *
```

METHOD FOR CLONING AND PRODUCING THE AVAI RESTRICTION ENDONUCLEASE IN E. COLI AND PURIFICATION OF THE RECOMBINANT AVAI RESTRICTION ENDONUCLEASE

BACKGROUND OF THE INVENTION

The present invention relates to the cloning and production of recombinant restriction endonuclease of AvaI.

Type II restriction endonucleases are a class of enzymes that occur naturally in bacteria. When they are purified away from other bacterial components, restriction endonucleases can be used in the laboratory to cleave DNA molecules into small fragments for generating recombinant DNA molecules.

Restriction endonucleases act by recognizing and binding to particular sequences of nucleotides along the DNA molecule. Once bound, they cleave the molecule within, to one side of, or to both sides of the recognition sequence. Different restriction endonucleases have affinity for different recognition sequences. Over two hundred and twenty restriction endonucleases with unique specificities have been identified among the many thousand of bacterial species that have been examined (Roberts and Macelis, Nucl. Acids Res. 26:338–350, (1998)).

Restriction endonucleases are named according to the bacteria from which they are derived. Thus, the species Deinococcus radiophilus for example, produces three different restriction endonucleases, named DraI, DraII and DraIII. These enzymes recognize and cleave the sequences 5'TTTAAA3', 5'PuGGNCCPy3' and 5'CACNNNGTG3' respectively. Escherichia coli RY13, on the other hand, produces only one enzyme, EcoRI, which recognizes the sequence 5'GAATTC3'.

A second component of bacterial restriction-modification (R-M) systems are the methylases. These enzymes provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (e.g., C5 methyl cytosine, N4 methyl cytosine, or N6 methyl adenine). Following methylation, the recognition sequence is no longer cleaved by the cognate restriction endonuclease. The DNA of a bacterial cell is fully modified and it is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is possible to clone genes and overproduce the enzymes they encode in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are cloned by a number of methods. The first cloned systems used bacteriophage infection as a means of selecting restriction endonuclease clones (EcoRII: Kosykh et al., Mol. Gen. Genet. 178:717–719 (1980); HhaII: Mann et al., Gene 3:97–112 (1978); PstI: Walder et al., Proc. Nat. Acad. Sci. 78:1503–1507 (1981)). Since the presence of restriction-modification systems in bacteria enable them to resist infection by bacteriophages, cells that carry cloned restriction-modification genes can, in principle, be selectively isolated as survivors from libraries that have been exposed to bacteriophages. However, it has been found that cloned restriction-modification genes do not always manifest sufficient phage resistance to confer selective survival.

Another cloning approach involves transferring systems initially characterized as plasmid-borne into E. coli cloning plasmids (EcoRV: Bougueleret et al., Nucl. Acids. Res. 12:3659–3676, (1984); PaeR7: Gingeras and Brooks, Proc. Natl. Acad. Sci. USA 80:402–406 (1983); Theriault and Roy, Gene 19:355–359 (1982); PvuII: Blumenthal et al., J. Bacteriol. 164:501–509, (1985)).

A third approach, and one that has been used to clone the majority of R-M systems, is by selection for an active methylase gene (U.S. Pat. No. 5,200,333 and BsuRI: Kiss et al., Nucl. Acids. Res. 13:6403–6421 (1985)). Since R and M genes are organized in close proximity to each other, both genes can often be cloned simultaneously. This selection does not always yield a complete restriction system however, but instead yields only the methylase gene (BspRI: Szomolanyi et al., Gene 10:219–225, (1980); BcnI: Janulaitis et al., Gene 20:197–204 (1982); BsuRI: Kiss and Baldauf, Gene 21:111–119 (1983); and MspI: Walder et al., J. Biol. Chem. 258:1235–1241, (1983)).

A more recent method, the "endo-blue method", has been described for direct cloning of restriction endonuclease genes in E. coli based on the indicator strain of E. coli containing the dinD::lacZ fusion (Fomenkov et al., U.S. Pat. No. 5,498,535); Fomenkov et al., Nucl. Acids Res. 22:2399–2403 (1994)). This method utilizes the E. coli SOS response following DNA damages caused by restriction endonucleases or non-specific nucleases. A number of thermostable nuclease genes (Tth111I, BsoBI, Tf nuclease) have been cloned by this method (U.S. Pat. No. 5,498,535).

Such recombinant enzymes are substantially pure and free of contaminants normally found in AvaI preparations made by conventional techniques from the native strain, such as that disclosed by Murray, et al., (Murray, et al., Biochem. J., 159:317–322 (1976)).

Because purified restriction endonucleases, and to a lesser extent, modification methylases, are useful tools for creating and analyzing DNA molecules in the laboratory, there is a commercial incentive to create bacterial strains through recombinant DNA techniques that produce these enzymes in large quantities. Such overexpression strains improve enzyme yield and simplify the task of enzyme purification.

It would, therefore, be desirable to purify AvaI restriction endonuclease to homogeneity, for use in medical diagnostic applications such as cancer gene mutation detection and pathogen detection by DNA amplification. It would further be desirable to develop a reproducible AvaI restriction enzyme purification procedure so as to meet the FDA purity standard required for the use of AvaI in such a diagnostic detection kit.

SUMMARY OF THE INVENTION

In accordance with the present invention there is provided a clone containing the gene coding for the AvaI restriction endonuclease derived from Anabaena variabilis (ATCC 27892). The present invention also relates to clones which express recombinant AvaI restriction endonuclease and BsoBI methylase and to methods for producing said enzymes. AvaI is an enzyme which recognizes the DNA sequence 5' C^YCGRG 3' and cleaves between the first and second bases, as indicated by the caret, on both strands leaving a 4 base, 5' extension. AvaI restriction endonuclease produced in accordance with the present invention is substantially pure and free of the contaminants normally found in AvaI preparations made by conventional techniques from the native strain, such as that disclosed by Murray, K. et al. (Murray, K. et al. Biochem. J. 159:317–322 (1976)).

The present invention, the cloning of DNA encoding the AvaI modification methylase and screening the resulting clones for endonuclease activity and subsequent overexpression of the AvaIR was achieved by methylase selection and the DNA sequencing of AvaIM and AvaIR genes isolated from the pUC19 HindIII clone as described herein. To highly express AvaI, it was then necessary to make an E. coli host pre-modified against AvaI digestion. Using an M.AvaI isoschizomer, the BsoBI methylase was expressed from a separate compatible plasmid in E. coli. A M.BsoBI pre-modified E. coli host was constructed which also protected against AvaI digestion.(Ruan, et al. Mol Gen Genet 252:695–699 (1996); Ruan, et al. Gene 188:35–39 (1977)). This E. coli host cell, was transformed with pRRS-AvaIR.

The avaIR gene was also expressed in a T7 expression vector pAII17 and the expression host was ER2504 [pACYC-BsoBIM, pAII17-AvaIR]. This clone, however, is not stable due to the constitutive expression of AvaI. To construct a stable overexpression clone, the bsoBIM gene was cloned into pLG339 carrying a pSC101 replication origin. A third plasmid, pLysS, was co-transformed into the T7 expression host to yield ER2504 [pLG-BsoBIM, pLysS, pAII17-AvaIR]. The overexpression clone produced approximately $6.4 \times 10^6$ units of AvaI per gram of wet E. coli cells.

DETAILED DESCRIPTION OF THE INVENTION

The present invention relates to the over-expression of recombinant AvaI as well as to vectors/host cells which produce recombinant AvaI. The AvaI restriction-modification system was cloned by a method which takes advantage of the fact that certain clones which are selected on the basis of containing and expressing the AvaI methylase gene also contain the AvaI restriction gene. The DNA of such clones is resistant to digestion, in vitro, by the AvaI restriction endonuclease. This resistance to digestion affords a means for selectively isolating clones encoding the AvaI methylase and restriction endonuclease.

The cloning of the AvaI R-M genes from Anabaena variabilis (ATCC 27892) into E. coli using partial genomic DNA libraries of A. variabilis were described in Lunnen et al., Gene 74:25–32 (1988).

In order to successfully overexpress AvaI from a clone, further steps beyond methylase selection were required including the use of an isoschizomer M.BsoBI. To protect E. coli DNA from AvaI digestion, a plasmid containing bsoBIM is used to modify an E. coli host and then cotransformed with a compatible expression plasmid pRRS+AvaIR followed by selection for colonies containing both recombinant plasmids on antibiotic Luria-Broth plates. The gene encoding M.BsoBI used to pre-modify DNA against AvaI endonuclease digestion has been described (Ruan et al, Gene, 188:35–39 (1977)).

The method described herein by which the AvaI restriction gene and methylase gene are preferably cloned and expressed includes the following steps:

1. The DNA of Anabaena variabilis is purified. Anabaena variabilis has been described in a number of publications including; Murray, K. et al, supra. Samples of this bacteria are available from American Type Culture Collection, Rockville, Md. (ATCC 27892).

2. The DNA is digested partially with restriction endonucleases such as HindIII, EcoRI, BamHI, PstI, and Sau3AI.

3. The digested DNAs from step 2 are ligated to a cloning vector, such as pBR322 and/or pUC19. The resulting mixture is used to transform an appropriate host such as E. coli K802 (ATCC 33526) cells. Note: since HindIII was the only digest to yield an active M.AvaI clone, the details for this work will be described.

4. The DNA/cell mixture is plated on antibiotic media selective for transformed cells, such as ampicillin. After incubation, the transformed colonies are collected together into a single culture, the primary cell library.

5. The recombinant plasmids are purified in toto from the primary cell library to make a primary plasmid library.

6. The plasmid library is then digested in vitro with the AvaI restriction endonuclease. AvaI restriction digestion causes the selective destruction of unmodified, non-methylase-containing, clones, resulting in an increase in the relative frequency of AvaI methylase-carrying clones. Bacterial Alkaline Phosphatase (BAP) was used to enhance the destruction of non-methylated clones.

7. Identification of AvaI methylase clones: The digested plasmid library DNA is transformed back into an E. coli host such as K802 (ATCC 33526), and transformed colonies are again obtained by plating on antibiotic plates. The colonies are picked and their DNA is analyzed for the presence of the AvaI modification in the following manner: The plasmid DNA is purified and incubated in vitro with AvaI restriction endonuclease to determine whether it is resistant to digestion by AvaI. The total cellular DNA (chromosomal and plasmid) of the clone can also be purified and incubated with AvaI restriction endonuclease. The DNA of clones that carry the AvaI methylase gene should be fully modified, and both the plasmid DNA and the total DNA should be found to be substantially, or completely resistant to digestion.

8. Clones carrying the AvaI restriction endonuclease are usually identified by preparing crude extracts of those clones identified in step 7 as carrying the AvaI methylase gene, and assaying the extracts for AvaI restriction endonuclease activity.

9. DNA sequence of the AvaI R-M system: The avaIM and avaIR genes were sequenced using various subclones of the 5.7 kb HindIII multi-fragment clone, pKL152RM 2-12. Plasmid DNA was sequenced by the dideoxy termination method using AmpliTaq DNA polymerase dye deoxy terminator sequencing kit and ABI373A automated DNA sequencer. Oligonucleotides were synthesized on the ABI394 DNA synthesizer (New England Biolabs, Beverly, Ma.).

10. Preparation of a BsoBI methylase pre-modified *E. coli* strain: The pACYC-BsoBIM plasmid was constructed as described (Ruan et al, supra (1996)). This bsoBIM gene was cloned into the BamHI site of pACYC184 and then transformed into *E. coli* strain ER2426 (NEB#974) and made competent by standard methods, in which the pACYC-BsoBIM plasmid would be selectable using chloramphenicol resistance. *E. coli* cells carrying this plasmid were fully resistant to BsoBI or AvaI cleavage, indicating sufficient BsoBI methylase expression in vivo.

11. Overexpression of AvaI: The avaIR gene is transferred to pRRS at the XbaI to XmaI sites under the control of the lac promoter. This is accomplished by amplification of a DNA fragment containing avaIR by PCR, the double digestion by the XbaI and XmaI endonucleases, followed by ligation into XbaI/XmaI digested pRRS plasmid. The pRRS plasmid is as described (Skoglund et al, *Gene* 88:1–5 (1990)). The DNA ligation mix was used to transform the M.BsoBI pre-modified *E. coli* ER2426. The colonies containing the two plasmids for both avaIR and bsoBIM were selected on ampicillin and chloramphenicol Luria Broth plates at 100 & 25 ug/ml respectively. Individual colonies were grown and the plasmids isolated were found to be resistant to AvaI endonuclease digestion and also contained the PCR fragment containing an intact avaIR gene. Endonuclease assays of crude extracts of these clones revealed a high level of AvaI ($8 \times 10^5$ units/g cells), a 40-fold increase over the original HindIII pUC19 clone pKL152RM 2-12 ($2 \times 10^4$ units/g cells).

12. Purification of the recombinant AvaI: The crude cell extract containing the AvaI restriction endonuclease activity is purified by affinity-chromatography, cation and anion exchange chromatography, and size exclusion chromatography. The chromatography steps are consisted of:

(a) Purification of AvaI through DNA binding protein affininy column such as Heparin hyper-D column, buffer pH 6.9, and pooling the peak fractions containing AvaI restriction endonuclease.

(b) Repeat step (a) for flow-through and wash fractions.

(c) Purification of AvaI through cation-exchange columns such as positively-charged Source 15Q column, and pooling the peak fractions containing AvaI restriction endonuclease.

(d) Purification of AvaI through DNA binding protein affininy column such as Heparin TSK column, and pooling the peak fractions containing AvaI restriction endonuclease.

(e) Purification of AvaI through size exclusion column such as Sephacryl S-100 26/60 column, and pooling the peak fractions containing AvaI restriction endonuclease.

(f) Purification of AvaI through anion-exchange column such as negatively-charged Source 15S column, and pooling the peak fractions containing AvaI restriction endonuclease.

(g) Purification of AvaI through DNA binding protein affininy column such as Heparin TSK (20 um) column, buffer pH 6.9, and pooling the peak fractions containing AvaI restriction endonuclease.

Figure 5:
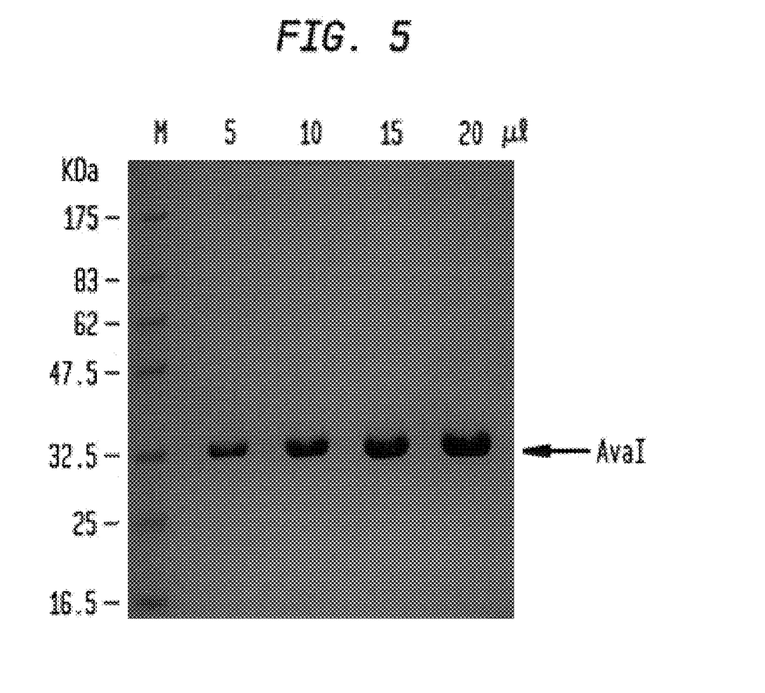
FIG. 5 illustrates SDS-PAGE of the purified recombinant AvaI restriction enzyme.
Figure 6:
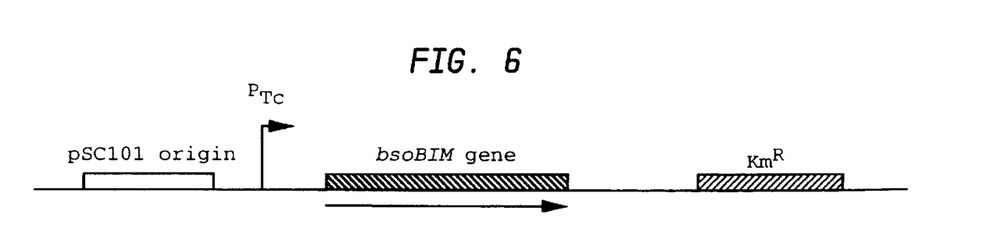
FIG. 6 illustrates a plasmid map of pLG-BsoBIM.

After purification through seven columns, the recombinant AvaI was purified to homogeneity. A single band of the expected MW of 35.6 kDa was detected on SDS-PAGE (FIG. 5).

13. Construction of a stable T7 overexpression clone: The bsoBIM gene was amplified by PCR and cloned into a vector pLG339 carrying the pSC101 replication origin. A third plasmid, pLysS, was co-transformed into the T7 expression host to yield ER2504 [pLG-BsoBIM, pLysS, pAII17-AvaIR]. This clone produces $6.4 \times 10^6$ units of AvaI per gram of wet *E. coli* cells.

Although the above-outlined steps represent the preferred mode for practicing the present invention, it will be apparent to those skilled in the art that the above described approach can vary in accordance with techniques known in the art.

The following Examples are given to illustrate embodiments of the present invention as it is presently preferred to be practiced. It will be understood that the Examples are illustrative, and that the invention is not to be considered as restricted thereto except as indicated in the appended claims.

The references cited above and below are herein incorporated by reference.

EXAMPLE 1

Cloning of AvaI Restriction Endonuclease Gene

1. DNA Purification:

To prepare genomic DNA of *Anabaena variabilis* (ATCC 27892), 1 gram of cell paste was resuspended in 5 ml of 0.1 M Tris-HCl, 0.1 M EDTA pH 7.6. The suspension was divided into two 2.5 ml portions. 3.5 ml of 1.7 mg/ml lysozyme in 0.1 M Tris-HCl, 0.1 M EDTA pH 7.6 was added to each portion and each was incubated for 15 minutes at 37° C. SDS was added to 1%, and proteinase K was added to 0.13 mg/ml and then the portions were incubated for 1 hour at 37° C. 0.4 ml of a solution of 10% SDS and 8% sarcosyl was added to each and incubation was continued at 55° C. for 2 hours. The two portions were then combined and dialysed against four changes of DNA buffer (10 mM Tris-HCl, 1 mM EDTA pH 8.0) for 24 hours. After the first dialysis, the DNA solution was centrifuged at 17,000 rpm for 10 minutes to remove solid debris. The clarified supernatant was returned to dialysis tubing and dialysis was continued. The dialysed DNA solution was then prepared for cesium chloride-ethidium bromide equilibrium density centrifugation by increasing the volume to 40 ml with DNA buffer, and then dividing the DNA solution into two 20 ml portions, to each of which 20 grams of cesium chloride and 0.2 ml of 5 mg/ml ethidium bromide were added. The DNA solution was centrifuged at 44,000 rpm for 48 hours and the resulting band of DNA was removed with a syringe and an 18 gauge needle. The ethidium bromide was removed by extracting 4 times with an equal volume of ice-cold, water-saturated N-butanol. The cesium chloride was removed by dialysis. The DNA was then precipitated with isopropyl alcohol and then redissolved in DNA buffer to a final concentration of approximately 200 ug/ml.

NOTE FOR STEPS 2–10: The details for constructing the HindIII library using pUC19 will be the only library described. EcoRI, BamHI, PstI, and Sau3AI libraries were also made, although only the pUC19+HindIII fragments library produced the AvaI restriction endonuclease.

2. Partial and Complete Digestion *A. variabilis* Genomic DNA:

5 ug of purified *A. variabilis* DNA was diluted into 250 ul of restriction endonuclease digestion buffer (10 mM Tris pH 7.5, 10 mM MgCl$_2$, 10 mM β-mercaptoethanol, 50 mM NaCl) and divided into one 100 ul tube and three 50 ul portions. 2.0 units of HindIII restriction endonuclease were added to 100 ul tube to achieve 1.0 units of enzyme per ug of DNA. 50 ul was withdrawn from the first tube and transferred to the second tube to achieve 0.5 HindIII units/ug, and so on, each succeeding tube receiving half of the previous amount of HindIII. The solutions were incubated at 37° C. for 1 hr. then the reactions were terminated by heating to 72° C. for 10 minutes and 10 ul from each was analyzed by agarose gel electrophoresis. Tubes exhibiting complete digestion were chosen as the source of complete digest fragments. (These were the 1.0 u/ug, 0.5 u/ug tubes) and tubes exhibiting partial digestion were chosen as the source for partial digest fragments for cloning. (These were the 0.25 u/ug, 0.125 u/ug tubes.) The solutions were mixed together and used as described below.

3. Ligation of Fragmented *A. variabilis* DNA to pUC19:

2.0 ug (75 ul) of HindIII partially-digested *A. variabilis* DNA was mixed with 1 ug (5 ul) of HindIII-cleaved and dephosphorylated pUC19. 10 ul of 10×ligation buffer (500 mM Tris pH 7.5, 100 mM $MgCl_2$, 100 mM DTT, 5 mM ATP), and 10 ul of sterile distilled water were added to bring the volume to 100 ul. 4 ul of T4 DNA ligase was added and the solution was incubated at 17° C. for 4 hours. The solution was sterilized by extraction with 20 ul of chloroform, then clarified by microcentifugation for 15 sec. 90 ul of the ligated DNA was used to transform *E. coli* strain K802 as follows: The DNA was mixed with 1.0 ml of SSC/CaCl2 (50 mM NaCl, 5 mM $Na_3$ Citrate, 67 mM $CaCl_2$) on ice and 1.0 ml of ice-cold competent *E. coli* K802 (ATCC 33526) cells were added. After a 6-minute incubation at 43° C., followed by 5 minutes on ice, the cells were diluted by the addition of 9 ml of Luria-broth (L-broth) then incubated at 37° C. for 4 hours.

4. Primary Cell Library:

The transformed cell culture was briefly centrifuged, the supernatant was discarded and the cells were resuspended in 1.0 ml of L-broth. 200 ul portions were plated onto Luria-agar (L-agar) plates containing 100 ug/ml ampicillin. After overnight incubation at 37° C., the plates were each flooded with 2.5 ml of 10 mM Tris, pH 7.5, 10 mM $MgCl_2$ and the transformed colonies were scraped together and pooled to form the primary cell library.

5. Primary Plasmid Library:

The primary plasmid library was prepared as follows: 2.5 ml of the primary cell library was inoculated into 500 ml of L-broth containing 100 ug/ml ampicillin. The culture was shaken overnight at 37° C. then centrifuged at 4,000 rpm for 5 minutes. The supernatant was discarded and the cell pellet was resuspended in 10 ml of 25% sucrose, 50 mM Tris, pH 8.0, at room temperature. 5 ml of 0.25 M EDTA, pH 8.0, was added, followed by 3 ml of 10 mg/ml lysozyme in 0.25 M Tris, pH 8.0. The solution was left on ice for 1 hour, then 12 ml of lytic mix (1% Triton X-100, 50 mM Tris, pH 8.0, 67 mM EDTA) was forcefully pipetted in, and the cell suspension gently swirled to achieve lysis. After lysis, the mixture was transferred to a 50 ml plastic centrifuge tube and spun at 17,000 rpm, 4° C. for 45 minutes. The supernatant was removed with a pipette. 20.0 gram of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two ⅝ in.×3 in. polyallomer centrifuge tubes and sealed. These tubes were then spun in a Beckman Ti70 rotor for 42 hours at 44,000 rpm, 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-Butanol. The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5 M NaCl was added to a final concentration of 0.4 M, then 2 volumes of isopropanol were added and mixed. The solution was stored overnight at −20° C. to precipitate the DNA. After precipitation, the solution was spun at 15,000 rpm, 4° C. for 15 minutes and the supernatant discarded. The tube was left on the bench to air-dry for 15 minutes, then the DNA pellet was dissolved in 500 ul of DNA buffer and stored at −20° C. The DNA concentration of plasmids prepared in this way were found to be 100 to 200 ug/ml.

6. Digestion of Plasmid Pool:

The primary plasmid pool was digested to destroy non-AvaI methylase clones as follows: The plasmid DNA was diluted to 30 ug/ml in 10 mM Tris pH 7.5, 10 MM $MgCl_2$,10 mM β-mercaptoethanol, 100 mM NaCl in a volume of 275 ul and divided into one 125 ul aliquot and two, 75 ul aliquots. To the 125 ul tube was added 12 ul units of AvaI to achieve 16.0 units of enzyme per ug of DNA. 25 ul was withdrawn from the first tube and transferred to the second tube to achieve 4.0 AvaI units/ug, and so on, each succeeding tube receiving half of the previous amount of AvaI. The tubes were incubated at 37° C. for 1 hour. The reactions were inactivated by heating to 72° C. for 10 minutes and 15 ul analysed by gel electrophoresis. 75 ul of each of the reaction mixtures was withdrawn. The DNA mixture was precipitated by the addition of 5 M NaCl and isopropanol. The precipitated DNA was collected by centrifugation and resuspended in 20 ul of DNA buffer (pH 9.0) to achieve approximately 150 ug DNA per ml. 0.2 units of bacterial alkaline phosphatase was added to each tube and each was incubated at 68° C. for two hours, under parafin oil. 80 ul of DNA buffer was added, mixed and removed. To this mixture 8 ul of chloroform was added and emulsified by vigorous mixing, and then separated by centrifugation.

7. Transformation:

12.5 ul of the BAP-treated DNA was used to transform *E. coli* strain K802 as follows: The DNA was mixed with 100 ul of SSC/CaCl2 (50 mM NaCl, 5 mM $Na_3$ Citrate, 67 mM $CaCl_2$) on ice and 100 ul of ice-cold competent *E.coli* K802 (ATCC 33526) cells were added. After a 3-minute incubation at 42° C., followed by 5 minutes on ice, the cells were diluted by the addition of 1 ml of Luria-broth (L-broth) then incubated at 37° C. for 1 hours. The cell/DNA mixtures were plated onto L-agar plates containing 100 ug/ml ampicillin. After overnight incubation at 37° C., the plates were examined. Digestion of the plasmid library with AvaI and bacterial alkaline phosphatase was found to have reduced the number of transformants by a factor of about $10^3$. 14 individual colonies were picked from the plates (16 units AvaI/ug). Each colony was inoculated into 10 ml of L-broth containing ampicillin, to prepare a miniculture, and was also streaked onto L-agar plates containing ampicillin to prepare a master stock.

8. Analysis of Surviving Individuals:

14 of the surviving colonies from the HindIII library obtained from section 7 were grown up into 10 ml cultures (section 7) and the plasmids that they carried were prepared by the following miniprep purification procedure, adapted from the method of Birnboin and Doly (Nucleic Acids Res. 7:1513–1523 (1979)).

Miniprep Procedure:

Each culture was centrifuged at 8,000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2 M NaOH, 1% SDS was added to each tube and the tubes were shaken to lyse the cells, then placed on ice. Once the solutions had cleared, 1.5 ml of 3 M sodium acetate, pH 4.8, was added to each and shaken. The precipitates that formed were spun down at 15,000 rpm, 4° C. for 10 minutes. Each supernatant was poured into a centrifuge tube containing 3 ml of isopropanol and mixed. After 10 minutes at room temperature, the tubes were spun at 15,000 rpm for 10 minutes to pellet the precipitated nucleic acids. The supernatants were discarded and the pellets were air-dried at room temperature for 30 minutes. Once dry, the pellets were resuspended in 850 ul of 10 mM Tris, 1 mM EDTA, pH 8.0. 75 ul of 5 M NaCl was added to each and the solutions were transferred to Eppendorf tubes containing 575 ul of isopropanol, and again precipitated for 10 minutes at room temperature. The tubes were then spun for 45 seconds in a microfuge, the supernatants were discarded and the pellets were air-dried. The pellets were then dissolved in 500 ul of 10 mM Tris, 1 mM EDTA, pH 8.0, containing 100 ug/ml RNase and incubated for 1 hour at 37° C. to digest the RNA. The DNA was precipitated once more by the addition of 50 ul of 5 M NaCl followed by 350 ul of isopropanol. After 10 minutes at room temperature, the DNA was spun down by centrifugation for 45 seconds, the supernatants were discarded and the pellets were redissolved in a final solution of 150 ul of 10 mM Tris 1 mM EDTA, pH 8.0. The plasmid minipreps were subsequently analyzed by digestion with AvaI.

AvaI Methylase Gene Clones:

The majority of the plasmids that were analyzed were found to be sensitive to digestion by AvaI endonuclease and to carry random fragments of A. variabilis DNA. These plasmids were spurious survivors, of no further interest, and were discarded. 6 out of 14 plasmids from the pUC19 HindIII library were found to be resistant to AvaI digestion and found to carry the same HindIII fragments of approximately 2.5, 1.5, 0.75, 0.70, and 0.45 Kb. These plasmids were subsequently shown to carry the AvaI modification methylase and restriction endonuclease activity. This was established by in vitro restriction endonuclease assays performed as follows:

To assay for endonuclease activity, two solutions were prepared: 10×restriction endonuclease buffer: 100 mM Tris, pH 7.5, 100 mM MgCl$_2$, 100 mM β-mercaptoethanol, 1,500 mM NaCl; and (ii) digestion reaction mix: 20 ul λDNA (500 ug/ml), 56 ul 10×restriction endonuclease buffer, 484 ul distilled water to achieve 50 ug/ml DNA. The cell extract was prepared as follows: A 50 ml culture of the clone to be tested was grown overnight in L-broth plus 100 ug/ml ampicillin at 37° C. and the cells were pelleted by centrifugation at 4,000 rpm for 5 minutes. The supernatant was discarded and the pellet was resuspended in 3 ml of sonication buffer (25 mM KPO$_4$ pH 7.5, 10 mM β-mercaptoethanol, 0.1 mM EDTA). Once resuspended, 0.5 ml of sonication buffer containing 10 mg/ml lysozyme was added. The suspension was swirled and left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract. To assay the extract, the digestion reaction mix was dispensed into 5 tubes, 150 ul into the first tube and 102.5 ul into each of the remaining 4 tubes. 7.5 ul of the extract was added to the first tube and mixed. 47.5 ul was removed from the first tube and transferred to the second tube, mixed and so on. The first tube thus received 3.75 ul of extract per ug of DNA, the second tube 1.25 ul/ug, the third tube, 0.4 ul/ug and so on. The tubes, each now containing 100 ul, were incubated at 37° C. for one hour, then a 20 ul sample of each was analyzed by gel electrophoresis. The titre of the extract was found to be approximately 5×10$^4$ units of AvaI restriction endonuclease per gram of wet cell paste. One such AvaI R-M clone was designated as pKL152RM 12-2.

Figure 1:
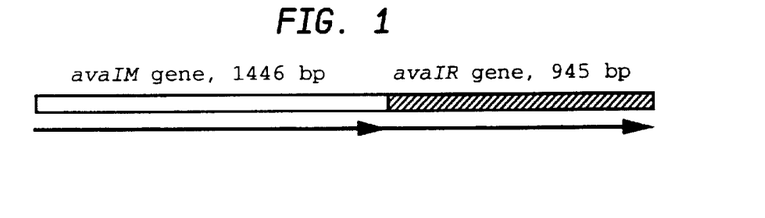
FIG. 1 illustrates gene organization of AvaI restriction-modification system.
Figure 2:
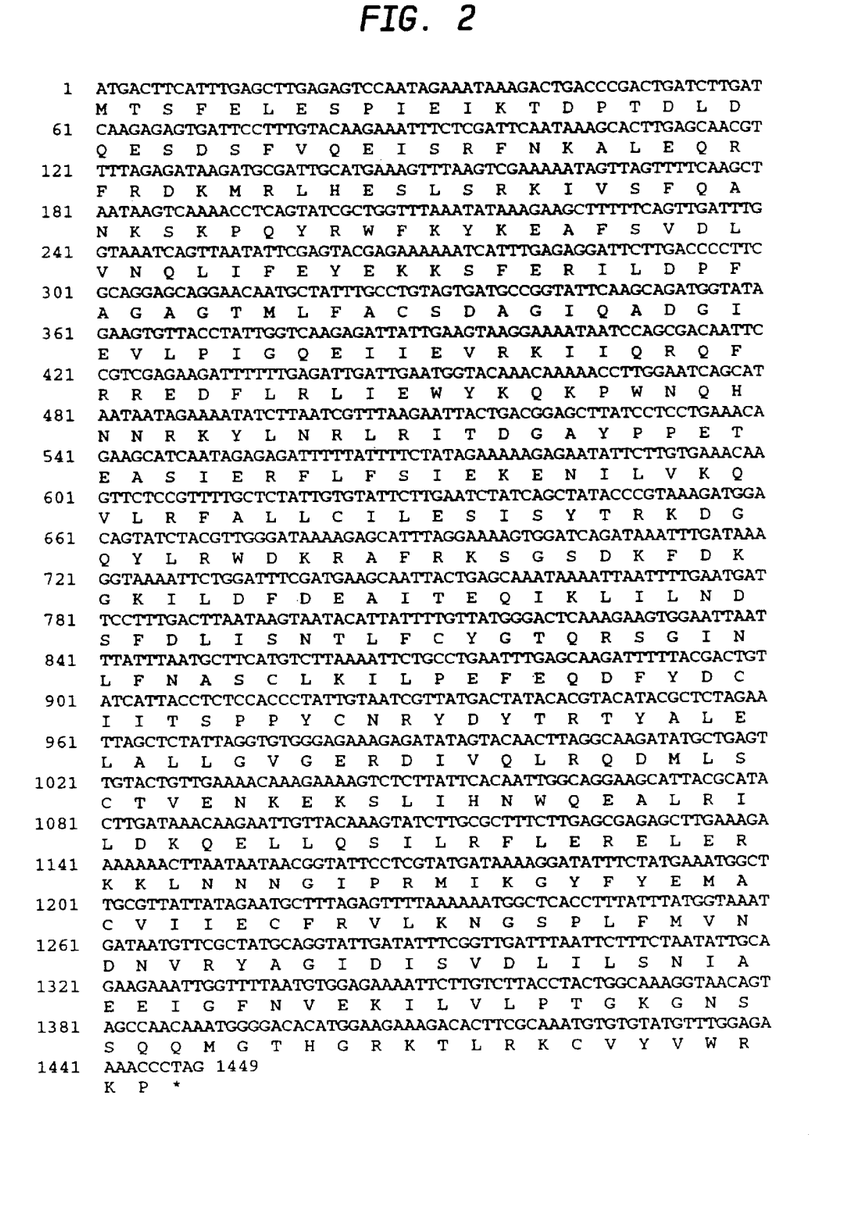
FIG. 2 shows the DNA sequence of avaIM gene (SEQ ID NO:1) and its predicted amino acid sequence (SEQ ID NO:2).
Figure 3:
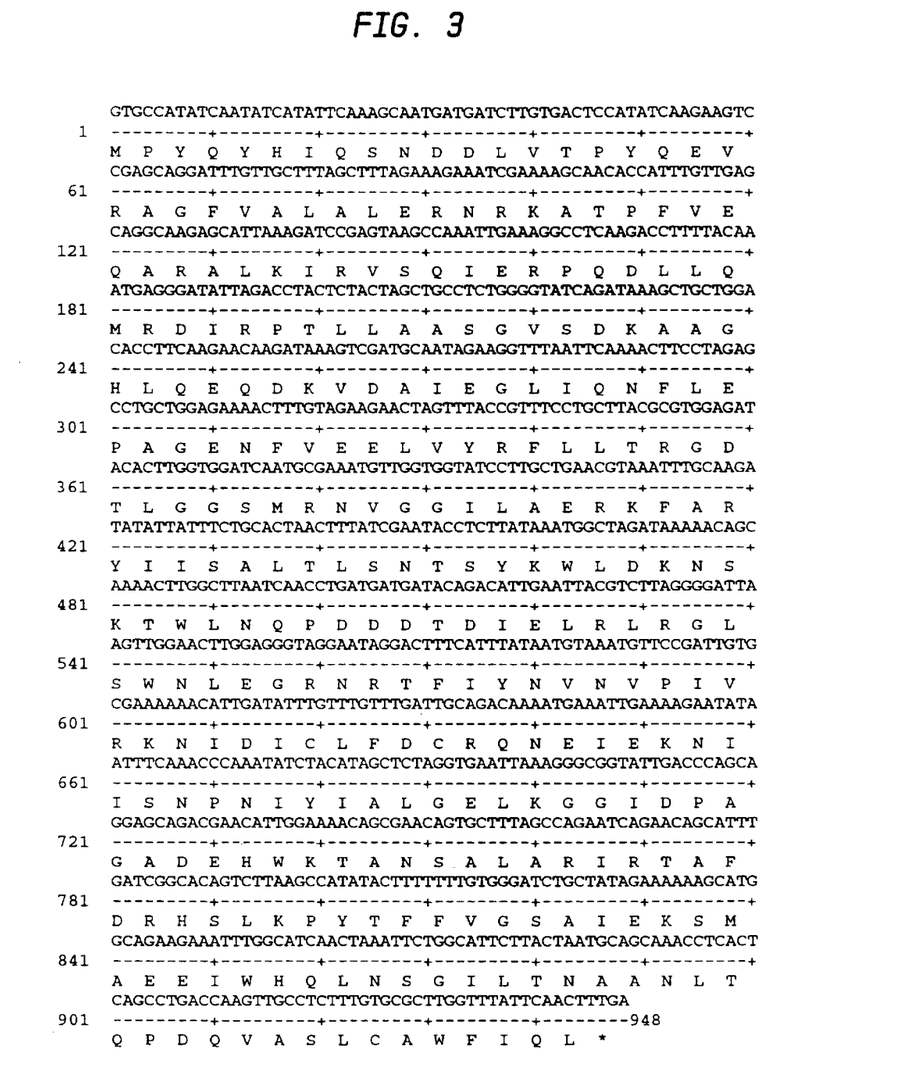
FIG. 3 shows DNA sequence of avaIR gene (SEQ ID NO:3) and its predicted amino acid sequence (SEQ ID NO:4).

9. DNA sequencing the avaIR and avaIM genes:

A restriction map of pKL152RM 2-12 containing the 5.7 kb HindIII multi-fragment was made and the location of the avaIM gene was determined by subcloning and deletions. A 2.7 kb XmnI/HincIII DNA fragment containing the AvaI R-M system was subcloned from an XmnI site within the 0.45 kb HindIII fragment to a HincII in the polylinker then cloned into the HincII site of another pUC19 plasmid. This clone was designated pKL152RM 2-12 X/H and sequenced by primer walking by the dideoxy termination method using AmpliTaq DNA polymerase dye deoxy terminator sequencing kit and ABI373A automated DNA sequencer. The nucleotide sequence revealed that the avaIM gene proceeds the avaIR gene. The gene organization of AvaI R-M system is shown in FIG. 1. The avaIM gene is 1,446 bp in length and codes for a protein of predicted MW of 56.5 kDa and has an aa sequence containing conserved motifs found in N4 cytosine methylases (FIG. 2; SEQ ID NO:1). The avaIR gene is 945 bp in length coding for an endonuclease of 35.6 kD (FIG. 3; SEQ ID NO:3).

EXAMPLE 2

Expression of AvaI restriction endonuclease using pRRS vector in E. coli

1. Preparation of a M.BsoBI Pre-modified E.coli Strain:

The plasmid carrying bsoBIM gene was constructed as described (Ruan et al, 1996) using PCR primers to bsoBIM gene. forward primer:

5'CGCGGATCCGGAGGTAAATAAGTG-
GAAACCGTACAAATGAGCTTGGAT TTAC 3'
(SEQ ID NO:5)

and the reverse primer:

5' CGCGGATCCCATGAAATCCTCTGTTCCT-
GCAAATATTCT 3' (SEQ ID NO:6)

The bsoBIM gene was amplified by PCR and was cloned into the Ba HI site of pACYC184 and then transformed into E.coli strain ER2426 (New England Biolabs Inc.#974) and made competent by standard methods, in which the pACYC-BsoBIM plasmid can be selected using chloramphenicol resistance. E. coli cells carrying this plasmid were fully resistant to BsoBI and AvaI cleavage.

2. Cloning of avaIR PCR Product

To overexpress AvaI endonuclease gene, a pUC19 derivative, pRRS was used as described (Skoglund et al, (1990)). The avaIR was amplified by PCR from the XmnI/HincII 2.7 kb pUC19 subclone pKL152RM 2-12 X/H. A forward primer included the translational start for avalr as well as a ribosome binding site preceded by two stop codons with an XbaI site for cloning into the polylinker of pRRS:

5'TTCTCTAGATAACGGTAGGAAGGAGAT-
CAAATGCCATATCAATATCAT ATTCAAAGC 3'
(SEQ ID NO:7).

The start codon for the endonuclease was changed from GTG to ATG. The reverse primer contained the 3' or carboxy end of avaIR with the stop codon and an XmaI site for cloning into PRRS:

5' TTCGGATCCCCGGGCTCAAAGT-TGAATAAACCAAGCGCAC 3' (SEQ ID NO:8)

The 0.95 kb fragment between the two primers was amplified by a PCR reaction using Vent® DNA polymerase (New England Biolabs, Beverly, Ma.) as follows: ten identical 100 ul reaction mixtures were set up as follows: 10 ul (1 ug) of pKL152RM 2-12 X/Hat 100 ug/ml was mixed with 20 ul of each forward and reverse primer each at 120 ug/ml respectively, 100 ul of dNTP's at a concentration of 4 mM for each nucleotide, 100 ul 10×Vent® Buffer (100 mM KCl, 200 mM Tris, pH 8.8, 100 mM $(NH_4)_2SO_4$, 20 mM $MgSO_4$, 1.0% Triton X-100) and 768 ul $dH_2O$ for a final volume of 990 ul. 10 reactions of 99 ul of primer/DNA mixture were dispensed followed by the addition of 1 ul of Vent® DNA polymerase at 2000 Units/ml to each PCR reaction. Samples were placed in the thermocycler (Perkin/Elmer Gene AMP PCR System 2400 (Emeryville, Calif.) at 95° C. 1 min, 54° C. 1 min, 72° C. 1 min for 30 cycles followed by electrophoresis on an agarose gel.

The PCR product was then purified for digestion by phenol/chloroform extraction followed by isopropanol precipitation. The PCR product was pelleted by microfuge centrifugation and resuspended in 180 ul 1×TE buffer and analyzed by gel electrophoresis. The avaIR PCR product was then digested with XbaI (30 units) and XmaI (3 units) endonucleases in a 50 ul reaction as follows: 5.0 ul of 10×Buffer (500 mM potassium acetate, 200 mM Tris-acetate, 100 mM magnesium acetate, 10 mM dithiothreitol (pH 7.9 @ 25° C.)), 0.5 ul of 10 ug/ml BSA, 5.0 ul avaIR PCR DNA (5 ug), 39.5 ul of $dH_2O$ followed by incubation at 37° C. for 1 hour and then 65° C. for 20 min. The digested PCR product was ligated to XbaI and XmaI-cut pRRS (0.5 ug) as follows: 2.5 ul of XbaI and XmaI digested pRRS plasmid was combined with 10 ul of XbaI and XmaI digested avaIR PCR reaction (described above), 5 ul of 10×ligation buffer (500 mM Tris pH 7.5, 100 mM $MgCl_2$, 100 mM DTT, 5 mM ATP), and 32 ul of sterile distilled water were added to bring the volume to 50 ul. 2 ul of T4 DNA ligase was added and the solution was incubated at 17° C. for overenight in a 50 ul ligation reaction. The ligation reaction was tranformed into the pre-modified M.BsoBI ER2426 *E. coli* strain. The DNA was mixed with 100 ul of $SSC/CaCl_2$ (50 mM NaCl, 5 mM $Na_3$Citrate, 67 mM $CaCl_2$) on ice and 200 ul of ice-cold competent *E. coli* cells were added. After a 3 minute incubation at 42° C., the cells were plated onto Luria-agar(L-agar) plates containing 100 ug/ml ampicillin and 25 ug/ml chloramphenicol and then incubated overnight at 37° C.

To identify the correct plasmid structure minipreps were made of 4 colonies. Two out of four contained the correct XbaI and XmaI avaIR PCR fragment as analysed by gel electrophoresis and were also shown to express AvaI endonuclease. The strain was designated NEB #992 *E. coli* ER2426 [pACYC184-BsoBIM, pRRS-AvaIR].

3. IPTG-induction of AvaI production in *E. coli*:

To overexpress AvaI from NEB #992 a 10 ml overnight culture was established at 37° C. no shaking in Luria Broth with ampicillin at 100 ug/ml and chloramphenicol at 25 ug/ml. One ml of overnight culture was diluted in 100 ml (100 fold) into LB containing described antibiotics and grown at 37° C. shaking to an $OD_{595}$ of 0.8 to 1.0. IPTG was added to 85 ug/ml to induce the synthesis of AvaI and the culture continued to grow approximately 3 more hours. The cells were pelleted by centrifugation at 4,000 rpm for 5 minutes. The supernatant was discarded and the pellet was resuspended in 6 ml of sonication buffer (20 mM $KPO_4$ pH 7.5, 100 mM NaCl, 10 mM β-ME, 0.1 mM EDTA) to a total volume of 7 ml. Once resuspended, 0.5 ml of sonication buffer containing 10 mg/ml lysozyme was added. The suspension was swirled and left on ice for 1 hour. A 1 ml sample was transferred to an Eppendorf tube and sonicated gently for three 10-second bursts to disrupt the cells. The tube was spun for 5 minutes in a microfuge and the supernatant was used as the cell extract. AvaI expression was established by in vitro restriction digestion of Lambda DNA for one hour at 37° C. in NEB buffer 4. To test the stability of the overexpression clone, 0.5 L to 1 L culture was grown to late log phase and IPTG was added to induce AvaI production. Cells were induced for 3 hours and cells were harvested by centrifugation. Cell pellet was resuspended in a sonication buffer and lysed by lysozyme treatment and sonication. Cell debris and insoluble materials were removed by centrifugation. AvaI restriction enzyme activity was assyed on Lambda DNA substrate by serial dilution of the cleared cell lysate. It was found that the overexpression clone produced about 5 to $8 \times 10^5$ units of AvaI/gram of wet cells under IPTG-induced condition.

EXAMPLE 3

Expression of AvaI using a T7 expression system

Two PCR primers were used to amplify avaIR gene using Vent® DNA polymerase. The two primers used here is the same as the two primers described in Example 2. They have the following sequences:

5'TTCTCTAGATAACGGTAGGAAGGAGAT-CAAATGCCATATCAATATCAT ATTCAAAGC3' (SEQ ID NO:9).

5' TTCGGATCCCCGGGCTCAAAGT-TGAATAAACCAAGCGCAC3' (SEQ ID NO:10).

The forward and reverse primers contain XbaI and BamHI sites respectively. PCR conditions were 95° C. for 5 min, 1 cycle; 95° C. for 1 min, 54° C. for 1 min, and 72° C. for 1 min for 20 cycles; and 72° C. for 5 min for 1 cycle. The PCR products were purified and cleaved with BamHI and XbaI for 4 h at 37° C. The digested PCR DNA was again purified and ligated to pET21at or pAII17 with compatible ends (BamHI & XbaI cut). The ligated DNA was used to transform M.BsoBI premodified competent cells of ER2504 [pACYC184-BsoBIM]. A total of 36 plasmid mini-preparations were made. Six isolates contain the avaIR gene in pAII17 and 16 isolates contain the avaIR gene insert in pET21at. Two isolates were grown in 0.5 L culture to late log phase and induced with IPTG at a final concentration 0.5 mM for 3 h. Cells were harvested and lysed by sonication and cell debris and insoluble fractions were removed by centrifugation. Cell extracts were diluted and assayed for AvaI activity on λ DNA. It was found that both clones produced about $6.5 \times 10^5$ units of AvaI/gram of wet cells.

This clone, however, is not very stable, probably as the result of leaky expression of non-induced cells. The XbaI site is immediately downstream of the T7 promoter and lac operator. The avaIR gene ligated to the XbaI site may interfere with Lac repressor binding.

To make a new stable clone, the avaIR gene was cloned into the NdeI and BamHI site of pAII17. The forward primer contains an NdeI site and has the following sequence:

5'GAAGGAGATCATATGCCATATCAATAT-CATATTCAAAGC3'

(SEQ ID NO:11).

The reverse primer contains a BamHI site and is the same as above. Thes two primers were used to amplify avaIR gene using Vent® DNA polymerase. PCR conditions were 95° C. for 5 min, 1 cycle; 95° C. for 1 min, 55° C. for 1 min, and 72° C. for 1 min for 20 cycles; and 72° C. for 5 min for 1 cycle. The PCR products were purified and cleaved with BamHI and NdeI for 12 h at 37° C. The digested PCR DNA was again purified and ligated to pAII17 with compatible ends (BamHI & NdeI cut). The ligated DNA was used to transform M.BsoBI premodified competent cells of ER2504 [pACYC184-BsoBIM]. A total of 12 plasmid mini-preparations were made. Seven isolates (#1, #5, #6, #7, #10, #11, and #12) contain the avaIR gene in pAII17. Isolates #5, #6, #10, #11, and #12 displayed high activity in cell extract made from 10 ml of IPTG-induced cells. Two isolates #10 and #12 were grown in 0.5 L cultures to late log phase and induced with IPTG at a final concentration 0.5 mM for 3 h. Cells were harvested and lysed by sonication and cell debris and insoluble fractions were removed by centrifugation. Cell extracts were diluted and assayed for AvaI activity on $\lambda$ DNA. It was found that both clones produced about 3 to $5 \times 10^5$ units of AvaI/gram of wet cells. The clone is not very stable and partial lysis ocurred in 0.5 L culture. The instability is probably caused by basal level of expression under non-induced condition.

Figure 4:
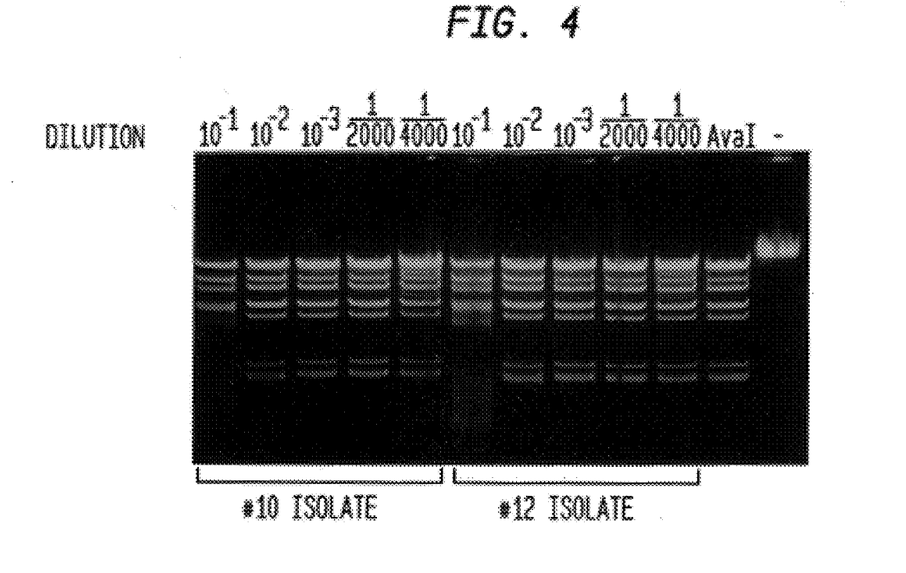
FIG. 4 illustrates AvaI restriction enzyme activity from E. coli cell extract.

To construct a stable T7 overexpression clone, the bsoBIM gene was amplified by PCR and cloned into a vector pLG339 carrying the pSC101 replication origin. The bsoBIM gene was under the control of Tc$^R$ promoter. A second plasmid, pLysS, was cotransformed into the T7 expression host to yield ER2504 [pLG-BsoBIM, pLysS]. It is known that T7 lysozyme inhibits the T7 RNA polymerase activity and thus can reduce the basal level of target gene expression. ER2504 [pLG-BsoBIM, pLysS] cells were made competent by CaCl$_2$ treatment and transformed with pAII17-AvaIR (an NdeI and BamHI fragment containing the avaIR gene). The resulting strain is ER2504 [pLG-BsoBIM, pLysS, pAII17-AvaIR]. 500 ml cultures of ER2504 [pLG-BsoBIM, pLysS, pAII17-AvaIR] were grown to late log phase (120–150 Klett units) and induced with IPTG at a final concentration 0.5 mM for 3 h. Cells were harvested and lysed by sonication and cell debris and insoluble fractions were removed by centrifugation. Cell extracts were diluted 10-, 100-, 1,000-, 2,000-, and 4,000-fold and 5 ul of the diluted extract was assayed for AvaI activity on $\lambda$ DNA (see FIG. 4). It was found that #10 and #12 clones produced about $6.4 \times 10^6$ units of AvaI/gram of wet cells. This is 128-fold more overexpression than the original clone. The strain ER2504 [pLG-BsoBIM, pLysS, pAII17-AvaIR] has been deposited under the terms and conditions of the Budapest Treaty with the American Type Culture Collection on Aug. 13, 1998 and received ATCC Accession No. 98837.

EXAMPLE 4

Purification of the Recombinant AvaI to Homogeneity

The crude cell extract containing the AvaI restriction endonuclease activity is purified by affinity-chromatography, ion-exchange chromatography, and size exclusion chromatography. The chromatography steps are consisted of:

(a) Purification of AvaI through DNA binding protein affininy column such as Heparin hyper-D column, buffer pH 6.9, and pooling the peak fractions containing AvaI restriction endonuclease.

(b) Repeating of step (a).

(c) Purification of AvaI through cation-exchange columns such as positively-charged Source 15Q column, and pooling the peak fractions containing AvaI restriction endonuclease.

(d) Purification of AvaI through DNA binding protein affinity column such as Heparin TSK column, and pooling the peak fractions containing AvaI restriction endonuclease.

(e) Purification of AvaI through size exclusion column such as Sephacryl S-100 26/60 column, and pooling the peak fractions containing AvaI restriction endonuclease.

(f) Purification of AvaI through anion-exchange column such as negatively-charged Source 15S column, and pooling the peak fractions containing AvaI restriction endonuclease.

(g) Purification of AvaI through DNA binding protein affinity column such as Heparin TSK (20 um) column, buffer pH 6.9, and pooling the peak fractions containing AvaI restriction endonuclease.

After purification through seven columns, the recombinant AvaI was purified to homogeneity. A single band of the expected MW of 35.6 kDa was detected on SDS-PAGE (FIG. 5).

The detailed AvaI purification procedure is described as following:

NEB #992 E. coli ER2426 [pACYC184-BsoBIM, PRRS-AvaIR] cells were grown in 100 liters of Fermentation Rich broth to late log phase. IPTG was added to a final concentration of 0.3 mM to induce AvaI production for 3 h. 466 grams of cells were harvested and resuspended in a buffer (50 mM NaCl, 20 mM KPO$_4$, pH 6.9, 0.1 mM EDTA, 10 mM β-ME, 5% glycerol). Cells were lysed by passing the cells through a Frech press (2k PSIG 1×, 12k PSIG 2×). A protease inhibitor cocktail (Sigma #P8465) was added to inhibit protease activity. The cell extract (1,950 ml total) was loaded onto a Heparin hyper-D column. The non DNA binding proteins were washed away with a buffer containing 50 mM NaCl, 20 mM KPO$_4$, pH 6.9, 0.1 mM EDTA, 10 mM β-ME, 5% glycerol. Proteins were eluted with 3 L of a 0.05 to 1 M NaCl gradient. Fractions 1 to 85 were assayed for AvaI restriction endonuclease activity by diluting the fractions 100-fold and used to cleave 1 ug of Lambda DNA for 30 sec. Fractions 37 to 55 contain high AvaI activity and these fractions were pooled. The flow-through and wash fractions also contained large amounts of AvaI (281 million units). So they were combined and reloaded onto the Heparin hyper-D column (Biosepra, Marlboro, Ma.). The elution condition was the same as above. A total of 850 ml of eluate containing AvaI were dialyzed against 10 L of a buffer containing 100 mM NaCl, 20 mM Tris, pH 7.8, 0.1 mM EDTA, 10 mM β-ME, 5% glycerol. The dialyzed eluate was diluted at 1:1 to 50 mM NaCl.

The diluted pool was loaded onto a Source 15Q column (Pharmacia, Piscataway, N.J.) pre-equilibrated with a buffer of 50 mM NaCl, 20 mM Tris, pH 7.8, 0.1 mM EDTA, 10 mM β-ME, 5% glycerol for cation exchange chromatography. The column was washed with a buffer of 50 mM NaCl, 20 mM Tris, pH 7.8, 0.1 mM EDTA, 10 mM β-ME, 5% glycerol. The fractions were assayed for AvaI activity. AvaI eluted at the salt concentration of approximately 225 mM Ncl. Those fractions #17 to 21 with AvaI activity were pooled and diluted to 50 mM NaCl.

The diluted fractions were loaded onto a Heparin-TSK column (Toso Haas, Montegomeryville, Pa.), washed with a buffer of 50 mM NaCl, 20 mM Tris, pH 7.8, 0.1 mM EDTA, 10 mM β-ME, 5% glycerol. Proteins were eluted with a salt gradient of 50 mM to 1 M NaCl. AvaI endonuclease was eluted at approximately 281 mM NaCl. Fractions 25 to 28 with AvaI activity were pooled and dialyzed in a buffer with 0.5 M NaCl, 20 mM Tris, pH 7.8, 0.1 mM EDTA, 10 mM β-ME, 5% glycerol.

The pooled fractions were loaded onto a size exclusion Sephacryl® S-100 26/60 column (Pharmacia, Piscataway, N.J.). The size exclusion column was run three times with 6–7 ml each. Fractions 51–58 with AvaI activity were pooled and diluted 10-fold in a buffer without NaCl.

The diluted fractions were loaded onto an anion exchange column Source 15S equilibrated with 50 mM NaCl. AvaI restriction endonuclease was found in the flow-through fractions.

The flow-through fractions were loaded onto a Heparin TSK column. The column was washed with a washing buffer containing 50 mM NaCl, 20 mM $KPO_4$, pH 6.9, 0.1 mM EDTA, 10 mM β-ME, 5% glycerol. AvaI protein was eluted with a 0.05 to 1 M NaCl gradient. Fractions 24 to 26 contained homogenous AvaI protein. Fractions 22 and 23 still contained two weak contaminating proteins. So fraction 22 and 23 were pooled, diluted to 50 mM NaCl and reloaded onto a Heparin TSK column. The column was washed and AvaI protein was eluted with a 0.05 to 1 M NaCl gradient. A total of 22 ml (20 mg) of homogenous recombinant AvaI protein was purified. The SDS-PAGE gel result is shown in FIG. 5.

What is claimed is:

1. A method for producing recombinant AvaI restriction endonuclease, said method comprising the steps of:
   (a) transforming a host cell with a first recombinant DNA vector containing the bsoBIM gene to generate a pre-modified host cell;
   (b) transforming said pre-modified host cell of step (a) with a second recombinant DNA vector containing the avaIR gene;
   (c) culturing said transformed pre-modified host cell of step (b) under conditions suitable for the overexpression of said second recombinant DNA vector; and
   (d) recovering the AvaI restriction endonuclease.

2. The method of claim 1, wherein step (b) further comprises co-transforming said pre-modified host cell of step (a) with a third recombinant DNA vector containing a gene encoding T7 lysozyme.

3. An *E. coli* host cell transformed by a first, a second and a third recombinant DNA vector, wherein said first recombinant DNA vector is pLG339-BsoIM, said second recombinant DNA vector is pAII17-AvaIR, and said third recombinant DNA vector is pLysS.

4. The transformed host cell of claim 3, wherein said transformed host cell is stable and capable of producing about 5,000,000 units of AvaI per gram of wet cells under IPTG-induced culture conditions.

5. The transformed host cell of claim 4, wherein said transformed host cell comprises ATCC Accession No. 98837.

* * * * *

UNITED STATES PATENT AND TRADEMARK OFFICE
CERTIFICATE OF CORRECTION

PATENT NO. : 6,004,793
DATED : December 21, 1999
INVENTOR(S) : Keith D. Lunnen, et. al.

It is certified that error appears in the above-identified patent and that said Letters Patent is hereby corrected as shown below:

| | | |
|---|---|---|
| Column 3, line 13 | replace "AvaIR" with --avaIR-- |
| Column 3, line 14 | replace "AvaIM and AvaIR" with --avaIM and avaIR-- |
| Column 3, line 22 | replace "(1977)" with --(1997)-- |
| Column 5, line 39 | replace "affininy" with --affinity-- |
| Column 5, line 48 | replace "affininy" with --affinity-- |
| Column 7, line 26 | replace "SSC/CaCl2" with --SSC/CaCl$_2$-- |
| Column 8, line 46 | replace "SSC/CaCl2" with --SSC/CaCl$_2$-- |
| Column 11, line 42 | replace "overenight" with --overnight-- |
| Column 11, line 48 | replace "agar(L-agar)" with --agar (L-agar)-- |
| Column 12, line 26 | replace "is" with --are-- |
| Column 12, line 62 | replace "(SEQ ID NO:11." With --(SEQ ID NO:11)-- |
| Column 12, line 64 | replace "Thes" with --These-- |
| Column 13, line 59 | replace "affininy" with --affinity-- |
| Column 14, line 21 | replace "following" with --follows-- |
| Column 14, line 57 | replace "Ncl" with --NC1-- |

UNITED STATES PATENT AND TRADEMARK OFFICE
CERTIFICATE OF CORRECTION

PATENT NO. : 6,004,793
DATED : December 21, 1999
INVENTOR(S) : Keith D. Lunnen, et. al.

It is certified that error appears in the above-identified patent and that said Letters Patent is hereby corrected as shown below:

```
Column 8, line 22    replace "10 MM" with --10 mM--
Column 10, line 51   replace "Ba HI" with --BamHI--
Column 10, line 62   replace "avalr" with --avaIR--
Column 11, line 4    replace "PRRS" with --pRRS--
Column 11, line 11   replace "X/Hat" with --X/H at--
Column 14, line 22   replace "PRRS-" with --pRRS---
```

Signed and Sealed this

Twenty-fourth Day of October, 2000

Attest:

Q. TODD DICKINSON

*Attesting Officer*       *Director of Patents and Trademarks*

SEQUENCE LISTING

<160> NUMBER OF SEQ ID NOS: 11

<210> SEQ ID NO 1
<211> LENGTH: 1449
<212> TYPE: DNA
<213> ORGANISM: Anabaena variabilis
<220> FEATURE:
<221> NAME/KEY: CDS
<222> LOCATION: (1)..(1446)

<400> SEQUENCE: 1

```
atg act tca ttt gag ctt gag agt cca ata gaa ata aag act gac ccg      48
Met Thr Ser Phe Glu Leu Glu Ser Pro Ile Glu Ile Lys Thr Asp Pro
 1               5                  10                  15 act gat ctt gat caa gag agt gat tcc ttt gta caa gaa att tct cga      96
Thr Asp Leu Asp Gln Glu Ser Asp Ser Phe Val Gln Glu Ile Ser Arg
             20                  25                  30 ttc aat aaa gca ctt gag caa cgt ttt aga gat aag atg cga ttg cat     144
Phe Asn Lys Ala Leu Glu Gln Arg Phe Arg Asp Lys Met Arg Leu His
         35                  40                  45 gaa agt tta agt cga aaa ata gtt agt ttt caa gct aat aag tca aaa     192
Glu Ser Leu Ser Arg Lys Ile Val Ser Phe Gln Ala Asn Lys Ser Lys
     50                  55                  60 cct cag tat cgc tgg ttt aaa tat aaa gaa gct ttt tca gtt gat ttg     240
Pro Gln Tyr Arg Trp Phe Lys Tyr Lys Glu Ala Phe Ser Val Asp Leu
 65                  70                  75                  80 gta aat cag tta ata ttc gag tac gag aaa aaa tca ttt gag agg att     288
Val Asn Gln Leu Ile Phe Glu Tyr Glu Lys Lys Ser Phe Glu Arg Ile
                 85                  90                  95 ctt gac ccc ttc gca gga gca gga aca atg cta ttt gcc tgt agt gat     336
Leu Asp Pro Phe Ala Gly Ala Gly Thr Met Leu Phe Ala Cys Ser Asp
            100                 105                 110 gcc ggt att caa gca gat ggt ata gaa gtg tta cct att ggt caa gag     384
Ala Gly Ile Gln Ala Asp Gly Ile Glu Val Leu Pro Ile Gly Gln Glu
        115                 120                 125 att att gaa gta agg aaa ata atc cag cga caa ttc cgt cga gaa gat     432
Ile Ile Glu Val Arg Lys Ile Ile Gln Arg Gln Phe Arg Arg Glu Asp
    130                 135                 140 ttt ttg aga ttg att gaa tgg tac aaa caa aaa cct tgg aat cag cat     480
Phe Leu Arg Leu Ile Glu Trp Tyr Lys Gln Lys Pro Trp Asn Gln His
145                 150                 155                 160 aat aat aga aaa tat ctt aat cgt tta aga att act gac gga gct tat     528
Asn Asn Arg Lys Tyr Leu Asn Arg Leu Arg Ile Thr Asp Gly Ala Tyr
                165                 170                 175 cct cct gaa aca gaa gca tca ata gag aga ttt tta ttt tct ata gaa     576
Pro Pro Glu Thr Glu Ala Ser Ile Glu Arg Phe Leu Phe Ser Ile Glu
            180                 185                 190 aaa gag aat att ctt gtg aaa caa gtt ctc cgt ttt gct cta ttg tgt     624
Lys Glu Asn Ile Leu Val Lys Gln Val Leu Arg Phe Ala Leu Leu Cys
```

|     |     |     |     |     |     |     |     |     |     |     |     |     |
| --- | --- | --- | --- | --- | --- | --- | --- | --- | --- | --- | --- | --- |
|     |     | 195 |     |     |     | 200 |     |     |     | 205 |     |     |
| att | ctt | gaa | tct | atc | agc | tat | acc | cgt | aaa | gat | gga | cag | tat | cta | cgt | 672 |
| Ile | Leu | Glu | Ser | Ile | Ser | Tyr | Thr | Arg | Lys | Asp | Gly | Gln | Tyr | Leu | Arg |     |
|     | 210 |     |     |     |     | 215 |     |     |     | 220 |     |     |     |     |     |     |
| tgg | gat | aaa | aga | gca | ttt | agg | aaa | agt | gga | tca | gat | aaa | ttt | gat | aaa | 720 |
| Trp | Asp | Lys | Arg | Ala | Phe | Arg | Lys | Ser | Gly | Ser | Asp | Lys | Phe | Asp | Lys |     |
| 225 |     |     |     |     | 230 |     |     |     |     | 235 |     |     |     |     | 240 |     |
| ggt | aaa | att | ctg | gat | ttc | gat | gaa | gca | att | act | gag | caa | ata | aaa | tta | 768 |
| Gly | Lys | Ile | Leu | Asp | Phe | Asp | Glu | Ala | Ile | Thr | Glu | Gln | Ile | Lys | Leu |     |
|     |     |     |     | 245 |     |     |     |     | 250 |     |     |     |     | 255 |     |     |
| att | ttg | aat | gat | tcc | ttt | gac | tta | ata | agt | aat | aca | tta | ttt | tgt | tat | 816 |
| Ile | Leu | Asn | Asp | Ser | Phe | Asp | Leu | Ile | Ser | Asn | Thr | Leu | Phe | Cys | Tyr |     |
|     |     |     | 260 |     |     |     |     | 265 |     |     |     |     | 270 |     |     |     |
| ggg | act | caa | aga | agt | gga | att | aat | tta | ttt | aat | gct | tca | tgt | ctt | aaa | 864 |
| Gly | Thr | Gln | Arg | Ser | Gly | Ile | Asn | Leu | Phe | Asn | Ala | Ser | Cys | Leu | Lys |     |
|     |     | 275 |     |     |     |     | 280 |     |     |     |     | 285 |     |     |     |     |
| att | ctg | cct | gaa | ttt | gag | caa | gat | ttt | tac | gac | tgt | atc | att | acc | tct | 912 |
| Ile | Leu | Pro | Glu | Phe | Glu | Gln | Asp | Phe | Tyr | Asp | Cys | Ile | Ile | Thr | Ser |     |
|     | 290 |     |     |     |     | 295 |     |     |     |     | 300 |     |     |     |     |     |
| cca | ccc | tat | tgt | aat | cgt | tat | gac | tat | aca | cgt | aca | tac | gct | cta | gaa | 960 |
| Pro | Pro | Tyr | Cys | Asn | Arg | Tyr | Asp | Tyr | Thr | Arg | Thr | Tyr | Ala | Leu | Glu |     |
| 305 |     |     |     |     | 310 |     |     |     |     | 315 |     |     |     |     | 320 |     |
| tta | gct | cta | tta | ggt | gtg | gga | gaa | aga | gat | ata | gta | caa | ctt | agg | caa | 1008 |
| Leu | Ala | Leu | Leu | Gly | Val | Gly | Glu | Arg | Asp | Ile | Val | Gln | Leu | Arg | Gln |     |
|     |     |     |     | 325 |     |     |     |     | 330 |     |     |     |     | 335 |     |     |
| gat | atg | ctg | agt | tgt | act | gtt | gaa | aac | aaa | gaa | aag | tct | ctt | att | cac | 1056 |
| Asp | Met | Leu | Ser | Cys | Thr | Val | Glu | Asn | Lys | Glu | Lys | Ser | Leu | Ile | His |     |
|     |     |     | 340 |     |     |     |     | 345 |     |     |     |     | 350 |     |     |     |
| aat | tgg | cag | gaa | gca | tta | cgc | ata | ctt | gat | aaa | caa | gaa | ttg | tta | caa | 1104 |
| Asn | Trp | Gln | Glu | Ala | Leu | Arg | Ile | Leu | Asp | Lys | Gln | Glu | Leu | Leu | Gln |     |
|     |     | 355 |     |     |     |     | 360 |     |     |     |     | 365 |     |     |     |     |
| agt | atc | ttg | cgc | ttt | ctt | gag | cga | gag | ctt | gaa | aga | aaa | aaa | ctt | aat | 1152 |
| Ser | Ile | Leu | Arg | Phe | Leu | Glu | Arg | Glu | Leu | Glu | Arg | Lys | Lys | Leu | Asn |     |
|     | 370 |     |     |     |     | 375 |     |     |     |     | 380 |     |     |     |     |     |
| aat | aac | ggt | att | cct | cgt | atg | ata | aaa | gga | tat | ttc | tat | gaa | atg | gct | 1200 |
| Asn | Asn | Gly | Ile | Pro | Arg | Met | Ile | Lys | Gly | Tyr | Phe | Tyr | Glu | Met | Ala |
| 385 |     |     |     |     | 390 |     |     |     |     | 395 |     |     |     |     | 400 |     |
| tgc | gtt | att | ata | gaa | tgc | ttt | aga | gtt | tta | aaa | aat | ggc | tca | cct | tta | 1248 |
| Cys | Val | Ile | Ile | Glu | Cys | Phe | Arg | Val | Leu | Lys | Asn | Gly | Ser | Pro | Leu |     |
|     |     |     |     | 405 |     |     |     |     | 410 |     |     |     |     | 415 |     |     |
| ttt | atg | gta | aat | gat | aat | gtt | cgc | tat | gca | ggt | att | gat | att | tcg | gtt | 1296 |
| Phe | Met | Val | Asn | Asp | Asn | Val | Arg | Tyr | Ala | Gly | Ile | Asp | Ile | Ser | Val |     |
|     |     |     | 420 |     |     |     |     | 425 |     |     |     |     | 430 |     |     |     |
| gat | tta | att | ctt | tct | aat | att | gca | gaa | gaa | att | ggt | ttt | aat | gtg | gag | 1344 |
| Asp | Leu | Ile | Leu | Ser | Asn | Ile | Ala | Glu | Glu | Ile | Gly | Phe | Asn | Val | Glu |     |
|     |     | 435 |     |     |     |     | 440 |     |     |     |     | 445 |     |     |     |     |
| aaa | att | ctt | gtc | tta | cct | act | ggc | aaa | ggt | aac | agt | agc | caa | caa | atg | 1392 |
| Lys | Ile | Leu | Val | Leu | Pro | Thr | Gly | Lys | Gly | Asn | Ser | Ser | Gln | Gln | Met |     |
|     | 450 |     |     |     |     | 455 |     |     |     |     | 460 |     |     |     |     |     |
| ggg | aca | cat | gga | aga | aag | aca | ctt | cgc | aaa | tgt | gtg | tat | gtt | tgg | aga | 1440 |
| Gly | Thr | His | Gly | Arg | Lys | Thr | Leu | Arg | Lys | Cys | Val | Tyr | Val | Trp | Arg |     |
| 465 |     |     |     |     | 470 |     |     |     |     | 475 |     |     |     |     | 480 |     |
| aaa | ccc | tag |     |     |     |     |     |     |     |     |     |     |     |     |     | 1449 |
| Lys | Pro |     |     |     |     |     |     |     |     |     |     |     |     |     |     |     |

<210> SEQ ID NO 2
<211> LENGTH: 482
<212> TYPE: PRT
<213> ORGANISM: Anabaena variabilis

<400> SEQUENCE: 2

```
Met Thr Ser Phe Glu Leu Glu Ser Pro Ile Glu Ile Lys Thr Asp Pro
  1               5                   10                  15

Thr Asp Leu Asp Gln Glu Ser Asp Ser Phe Val Gln Glu Ile Ser Arg
              20                  25                  30

Phe Asn Lys Ala Leu Glu Gln Arg Phe Arg Asp Lys Met Arg Leu His
          35                  40                  45

Glu Ser Leu Ser Arg Lys Ile Val Ser Phe Gln Ala Asn Lys Ser Lys
      50                  55                  60

Pro Gln Tyr Arg Trp Phe Lys Tyr Lys Glu Ala Phe Ser Val Asp Leu
 65              70                  75                      80

Val Asn Gln Leu Ile Phe Glu Tyr Glu Lys Lys Ser Phe Glu Arg Ile
              85                  90                  95

Leu Asp Pro Phe Ala Gly Ala Gly Thr Met Leu Phe Ala Cys Ser Asp
             100                 105                 110

Ala Gly Ile Gln Ala Asp Gly Ile Glu Val Leu Pro Ile Gly Gln Glu
         115                 120                 125

Ile Ile Glu Val Arg Lys Ile Ile Gln Arg Gln Phe Arg Arg Glu Asp
     130                 135                 140

Phe Leu Arg Leu Ile Glu Trp Tyr Lys Gln Lys Pro Trp Asn Gln His
145                 150                 155                 160

Asn Asn Arg Lys Tyr Leu Asn Arg Leu Arg Ile Thr Asp Gly Ala Tyr
             165                 170                 175

Pro Pro Glu Thr Glu Ala Ser Ile Glu Arg Phe Leu Phe Ser Ile Glu
             180                 185                 190

Lys Glu Asn Ile Leu Val Lys Gln Val Leu Arg Phe Ala Leu Leu Cys
             195                 200                 205

Ile Leu Glu Ser Ile Ser Tyr Thr Arg Lys Asp Gly Gln Tyr Leu Arg
     210                 215                 220

Trp Asp Lys Arg Ala Phe Arg Lys Ser Gly Ser Asp Lys Phe Asp Lys
225                 230                 235                 240

Gly Lys Ile Leu Asp Phe Asp Glu Ala Ile Thr Glu Gln Ile Lys Leu
             245                 250                 255

Ile Leu Asn Asp Ser Phe Asp Leu Ile Ser Asn Thr Leu Phe Cys Tyr
             260                 265                 270

Gly Thr Gln Arg Ser Gly Ile Asn Leu Phe Asn Ala Ser Cys Leu Lys
         275                 280                 285

Ile Leu Pro Glu Phe Glu Gln Asp Phe Tyr Asp Cys Ile Ile Thr Ser
     290                 295                 300

Pro Pro Tyr Cys Asn Arg Tyr Asp Tyr Thr Arg Thr Tyr Ala Leu Glu
305                 310                 315                 320

Leu Ala Leu Leu Gly Val Gly Glu Arg Asp Ile Val Gln Leu Arg Gln
             325                 330                 335

Asp Met Leu Ser Cys Thr Val Glu Asn Lys Glu Lys Ser Leu Ile His
             340                 345                 350

Asn Trp Gln Glu Ala Leu Arg Ile Leu Asp Lys Gln Glu Leu Leu Gln
         355                 360                 365

Ser Ile Leu Arg Phe Leu Glu Arg Glu Leu Glu Arg Lys Lys Leu Asn
     370                 375                 380

Asn Asn Gly Ile Pro Arg Met Ile Lys Gly Tyr Phe Tyr Glu Met Ala
385                 390                 395                 400

Cys Val Ile Ile Glu Cys Phe Arg Val Leu Lys Asn Gly Ser Pro Leu
             405                 410                 415

Phe Met Val Asn Asp Asn Val Arg Tyr Ala Gly Ile Asp Ile Ser Val
```

|       |     | 420 |     |     |     | 425 |     |     |     | 430 |     |     |
|-------|-----|-----|-----|-----|-----|-----|-----|-----|-----|-----|-----|-----|
| Asp | Leu | Ile | Leu | Ser | Asn | Ile | Ala | Glu | Glu | Ile | Gly | Phe | Asn | Val | Glu |
|     |     |     | 435 |     |     |     | 440 |     |     |     | 445 |     |

Lys Ile Leu Val Leu Pro Thr Gly Lys Gly Asn Ser Ser Gln Gln Met
450                     455                 460

Gly Thr His Gly Arg Lys Thr Leu Arg Lys Cys Val Tyr Val Trp Arg
465                 470                 475                 480

Lys Pro

<210> SEQ ID NO 3
<211> LENGTH: 948
<212> TYPE: DNA
<213> ORGANISM: Anabaena variabilis
<220> FEATURE:
<221> NAME/KEY: CDS
<222> LOCATION: (1)..(945)

<400> SEQUENCE: 3

```
gtg cca tat caa tat cat att caa agc aat gat gat ctt gtg act cca      48
Val Pro Tyr Gln Tyr His Ile Gln Ser Asn Asp Asp Leu Val Thr Pro
 1               5                  10                  15 tat caa gaa gtc cga gca gga ttt gtt gct tta gct tta gaa aga aat      96
Tyr Gln Glu Val Arg Ala Gly Phe Val Ala Leu Ala Leu Glu Arg Asn
             20                  25                  30 cga aaa gca aca cca ttt gtt gag cag gca aga gca tta aag atc cga     144
Arg Lys Ala Thr Pro Phe Val Glu Gln Ala Arg Ala Leu Lys Ile Arg
         35                  40                  45 gta agc caa att gaa agg cct caa gac ctt tta caa atg agg gat att     192
Val Ser Gln Ile Glu Arg Pro Gln Asp Leu Leu Gln Met Arg Asp Ile
     50                  55                  60 aga cct act cta cta gct gcc tct ggg gta tca gat aaa gct gct gga     240
Arg Pro Thr Leu Leu Ala Ala Ser Gly Val Ser Asp Lys Ala Ala Gly
 65                  70                  75                  80 cac ctt caa gaa caa gat aaa gtc gat gca ata gaa ggt tta att caa     288
His Leu Gln Glu Gln Asp Lys Val Asp Ala Ile Glu Gly Leu Ile Gln
                 85                  90                  95 aac ttc cta gag cct gct gga gaa aac ttt gta gaa gaa cta gtt tac     336
Asn Phe Leu Glu Pro Ala Gly Glu Asn Phe Val Glu Glu Leu Val Tyr
            100                 105                 110 cgt ttc ctg ctt acg cgt gga gat aca ctt ggt gga tca atg cga aat     384
Arg Phe Leu Leu Thr Arg Gly Asp Thr Leu Gly Gly Ser Met Arg Asn
        115                 120                 125 gtt ggt ggt atc ctt gct gaa cgt aaa ttt gca aga tat att att tct     432
Val Gly Gly Ile Leu Ala Glu Arg Lys Phe Ala Arg Tyr Ile Ile Ser
    130                 135                 140 gca cta act tta tcg aat acc tct tat aaa tgg cta gat aaa aac agc     480
Ala Leu Thr Leu Ser Asn Thr Ser Tyr Lys Trp Leu Asp Lys Asn Ser
145                 150                 155                 160 aaa act tgg ctt aat caa cct gat gat gat aca gac att gaa tta cgt     528
Lys Thr Trp Leu Asn Gln Pro Asp Asp Asp Thr Asp Ile Glu Leu Arg
                165                 170                 175 ctt agg gga tta agt tgg aac ttg gag ggt agg aat agg act ttc att     576
Leu Arg Gly Leu Ser Trp Asn Leu Glu Gly Arg Asn Arg Thr Phe Ile
            180                 185                 190 tat aat gta aat gtt ccg att gtg cga aaa aac att gat att tgt ttg     624
Tyr Asn Val Asn Val Pro Ile Val Arg Lys Asn Ile Asp Ile Cys Leu
        195                 200                 205 ttt gat tgc aga caa aat gaa att gaa aag aat ata att tca aac cca     672
Phe Asp Cys Arg Gln Asn Glu Ile Glu Lys Asn Ile Ile Ser Asn Pro
    210                 215                 220
```

-continued

| | | |
|---|---|---|
| aat atc tac ata gct cta ggt gaa tta aag ggc ggt att gac cca gca<br>Asn Ile Tyr Ile Ala Leu Gly Glu Leu Lys Gly Gly Ile Asp Pro Ala<br>225                           230                             235                           240 | 720 |
| gga gca gac gaa cat tgg aaa aca gcg aac agt gct tta gcc aga atc<br>Gly Ala Asp Glu His Trp Lys Thr Ala Asn Ser Ala Leu Ala Arg Ile<br>                       245                           250                           255 | 768 |
| aga aca gca ttt gat cgg cac agt ctt aag cca tat act ttt ttt gtg<br>Arg Thr Ala Phe Asp Arg His Ser Leu Lys Pro Tyr Thr Phe Phe Val<br>             260                           265                          270 | 816 |
| gga tct gct ata gaa aaa agc atg gca gaa gaa att tgg cat caa cta<br>Gly Ser Ala Ile Glu Lys Ser Met Ala Glu Glu Ile Trp His Gln Leu<br>        275                         280                           285 | 864 |
| aat tct ggc att ctt act aat gca gca aac ctc act cag cct gac caa<br>Asn Ser Gly Ile Leu Thr Asn Ala Ala Asn Leu Thr Gln Pro Asp Gln<br>290                           295                             300 | 912 |
| gtt gcc tct ttg tgc gct tgg ttt att caa ctt tga<br>Val Ala Ser Leu Cys Ala Trp Phe Ile Gln Leu<br>305                           310                           315 | 948 |

<210> SEQ ID NO 4
<211> LENGTH: 315
<212> TYPE: PRT
<213> ORGANISM: Anabaena variabilis

<400> SEQUENCE: 4

Val Pro Tyr Gln Tyr His Ile Gln Ser Asn Asp Asp Leu Val Thr Pro
1                        5                        10                     15

Tyr Gln Glu Val Arg Ala Gly Phe Val Ala Leu Ala Leu Glu Arg Asn
                   20                       25                        30

Arg Lys Ala Thr Pro Phe Val Glu Gln Ala Arg Ala Leu Lys Ile Arg
               35                      40                         45

Val Ser Gln Ile Glu Arg Pro Gln Asp Leu Leu Gln Met Arg Asp Ile
    50                        55                        60

Arg Pro Thr Leu Leu Ala Ala Ser Gly Val Ser Asp Lys Ala Ala Gly
65                        70                        75                        80

His Leu Gln Glu Gln Asp Lys Val Asp Ala Ile Glu Gly Leu Ile Gln
                   85                       90                        95

Asn Phe Leu Glu Pro Ala Gly Glu Asn Phe Val Glu Glu Leu Val Tyr
               100                      105                      110

Arg Phe Leu Leu Thr Arg Gly Asp Thr Leu Gly Gly Ser Met Arg Asn
           115                      120                      125

Val Gly Gly Ile Leu Ala Glu Arg Lys Phe Ala Arg Tyr Ile Ile Ser
       130                      135                      140

Ala Leu Thr Leu Ser Asn Thr Ser Tyr Lys Trp Leu Asp Lys Asn Ser
145                      150                        155                      160

Lys Thr Trp Leu Asn Gln Pro Asp Asp Thr Asp Ile Glu Leu Arg
                   165                      170                      175

Leu Arg Gly Leu Ser Trp Asn Leu Glu Gly Arg Asn Arg Thr Phe Ile
           180                      185                      190

Tyr Asn Val Asn Val Pro Ile Val Arg Lys Asn Ile Asp Ile Cys Leu
       195                      200                      205

Phe Asp Cys Arg Gln Asn Glu Ile Glu Lys Asn Ile Ile Ser Asn Pro
    210                        215                        220

Asn Ile Tyr Ile Ala Leu Gly Glu Leu Lys Gly Gly Ile Asp Pro Ala
225                      230                        235                      240

Gly Ala Asp Glu His Trp Lys Thr Ala Asn Ser Ala Leu Ala Arg Ile
                   245                      250                      255

```
Arg Thr Ala Phe Asp Arg His Ser Leu Lys Pro Tyr Thr Phe Phe Val
            260                 265                 270

Gly Ser Ala Ile Glu Lys Ser Met Ala Glu Glu Ile Trp His Gln Leu
        275                 280                 285

Asn Ser Gly Ile Leu Thr Asn Ala Ala Asn Leu Thr Gln Pro Asp Gln
    290                 295                 300

Val Ala Ser Leu Cys Ala Trp Phe Ile Gln Leu
305                 310                 315

<210> SEQ ID NO 5
<211> LENGTH: 52
<212> TYPE: DNA
<213> ORGANISM: Bacillus stearothermophilus

<400> SEQUENCE: 5
cgcggatccg gaggtaaata agtggaaacc gtacaaatga gcttggattt ac          52

<210> SEQ ID NO 6
<211> LENGTH: 39
<212> TYPE: DNA
<213> ORGANISM: Bacillus stearothermophilus

<400> SEQUENCE: 6
cgcggatccc atgaaatcct ctgttcctgc aaatattct                         39

<210> SEQ ID NO 7
<211> LENGTH: 57
<212> TYPE: DNA
<213> ORGANISM: Anabaena variabilis

<400> SEQUENCE: 7
ttctctagat aacggtagga aggagatcaa atgccatatc aatatcatat tcaaagc     57

<210> SEQ ID NO 8
<211> LENGTH: 40
<212> TYPE: DNA
<213> ORGANISM: Anabaena variabilis

<400> SEQUENCE: 8
ttcggatccc cgggctcaaa gttgaataaa ccaagcgcac                        40

<210> SEQ ID NO 9
<211> LENGTH: 57
<212> TYPE: DNA
<213> ORGANISM: Anabaena variabilis

<400> SEQUENCE: 9
ttctctagat aacggtagga aggagatcaa atgccatatc aatatcatat tcaaagc     57

<210> SEQ ID NO 10
<211> LENGTH: 40
<212> TYPE: DNA
<213> ORGANISM: Anabaena variabilis

<400> SEQUENCE: 10
ttcggatccc cgggctcaaa gttgaataaa ccaagcgcac                        40

<210> SEQ ID NO 11
<211> LENGTH: 39
<212> TYPE: DNA
<213> ORGANISM: Anabaena variabilis

<400> SEQUENCE: 11
```

| | |
|---|---|
| gaaggagatc atatgccata tcaatatcat attcaaagc | 39 |